(12) United States Patent
Dua

(10) Patent No.: US 12,405,960 B2
(45) Date of Patent: Sep. 2, 2025

(54) METHODS AND SYSTEMS FOR DETERMINING A PRIORITY FOR PROCESSING OF SELECTED DATABASE RECORDS

(71) Applicant: Ensemble RCM, LLC, Cincinnati, OH (US)

(72) Inventor: Luv Dua, Livingston, NJ (US)

(73) Assignee: Ensemble RCM, LLC, Cincinnati, OH (US)

( * ) Notice: Subject to any disclaimer, the term of this patent is extended or adjusted under 35 U.S.C. 154(b) by 0 days.

(21) Appl. No.: 18/428,689

(22) Filed: Jan. 31, 2024

(65) Prior Publication Data
US 2025/0245234 A1    Jul. 31, 2025

(51) Int. Cl.
*G06F 16/2457* (2019.01)
*G16H 40/20* (2018.01)

(52) U.S. Cl.
CPC ....... *G06F 16/24578* (2019.01); *G16H 40/20* (2018.01)

(58) Field of Classification Search
CPC .......................... G06F 16/24578; G16H 40/20
USPC .......................................................... 707/723
See application file for complete search history.

(56) References Cited

U.S. PATENT DOCUMENTS

| | | | | |
|---|---|---|---|---|
| 9,830,148 | B1* | 11/2017 | Mo | G06F 8/77 |
| 2008/0288294 | A1* | 11/2008 | Eisenberger | G06Q 30/0601 705/3 |
| 2019/0266269 | A1* | 8/2019 | Schouten | G06F 16/2365 |
| 2020/0012730 | A1* | 1/2020 | Schouten | G06F 16/17 |
| 2022/0083532 | A1* | 3/2022 | Solari | G06N 5/04 |
| 2024/0257045 | A1* | 8/2024 | Wang | G06Q 10/087 |

* cited by examiner

*Primary Examiner* — Michael Pham
(74) *Attorney, Agent, or Firm* — Sheridan Ross P.C.

(57) ABSTRACT

Embodiments of the present disclosure are directed to methods and systems for the processing of database records. Processing database records can comprise maintaining a records in a database. A subset of records from the plurality of records can be identified for further process, e.g., based on a value stored in a field of each record. Each record of the identified subset of records can be scored based on a plurality of factors related to each record of the identified subset of records. The identified subset of records can then be prioritized into an ordered list of records based on the score for each record of the identified subset of records and one or more workflows can be executed on the identified subset of records based on the ordered list of records.

20 Claims, 6 Drawing Sheets

METHODS AND SYSTEMS FOR DETERMINING A PRIORITY FOR PROCESSING OF SELECTED DATABASE RECORDS

FIELD OF THE DISCLOSURE

Embodiments of the present disclosure relate generally to methods and systems for managing transaction records in a database and more particularly to determining a priority for processing of selected database records.

Figure 1:
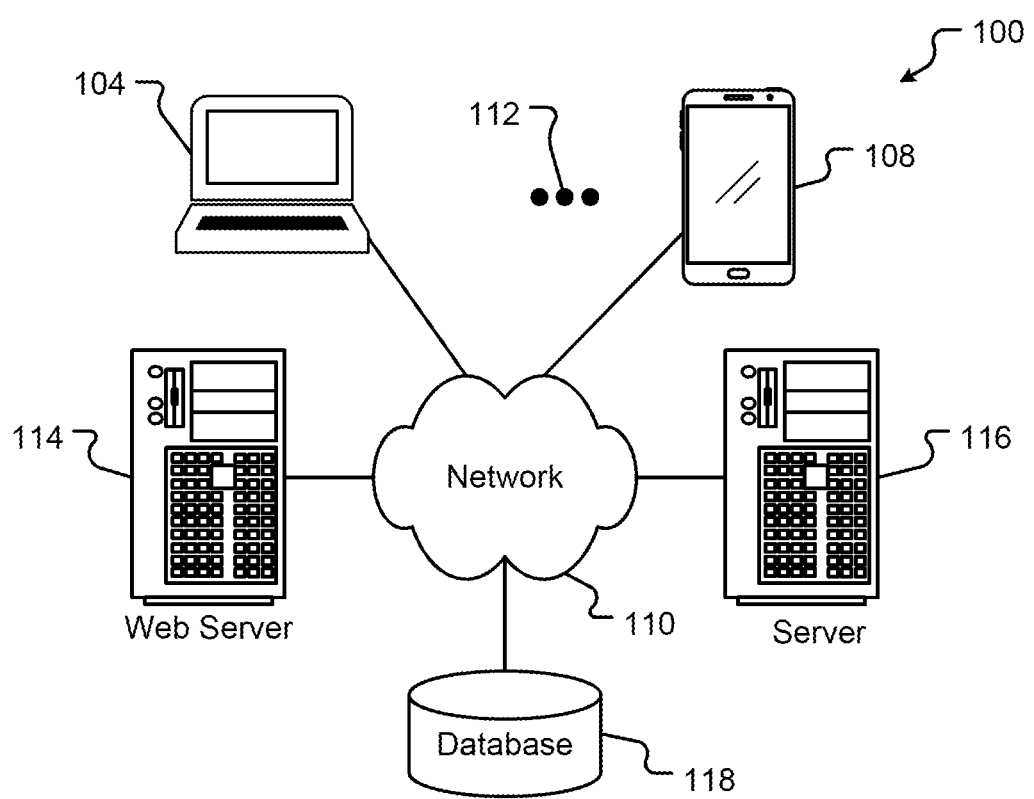
FIG. 1 is a block diagram illustrating elements of an exemplary computing environment in which embodiments of the present disclosure may be implemented.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

DETAILED DESCRIPTION

In the following description, for the purposes of explanation, numerous specific details are set forth in order to provide a thorough understanding of various embodiments disclosed herein. It will be apparent, however, to one skilled in the art that various embodiments of the present disclosure may be practiced without some of these specific details. The ensuing description provides exemplary embodiments only, and is not intended to limit the scope or applicability of the disclosure. Furthermore, to avoid unnecessarily obscuring the present disclosure, the preceding description omits a number of known structures and devices. This omission is not to be construed as a limitation of the scopes of the claims. Rather, the ensuing description of the exemplary embodiments will provide those skilled in the art with an enabling description for implementing an exemplary embodiment. It should however be appreciated that the present disclosure may be practiced in a variety of ways beyond the specific detail set forth herein.

While the exemplary aspects, embodiments, and/or configurations illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices or collocated on a particular node of a distributed network, such as an analog and/or digital telecommunications network, a packet-switch network, or a circuit-switched network. It will be appreciated from the following description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

As used herein, the phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The term "computer-readable medium" as used herein refers to any tangible storage and/or transmission medium that participate in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

A "computer readable signal" medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable medium may be transmitted using any appropriate medium, including but not limited to wireless, wireline, optical fiber cable, RF, etc., or any suitable combination of the foregoing.

The terms "determine," "calculate," and "compute," and variations thereof, as used herein, are used interchangeably and include any type of methodology, process, mathematical operation or technique.

It shall be understood that the term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the disclosure, brief description of the drawings, detailed description, abstract, and claims themselves.

Aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Any combination of one or more computer readable medium(s) may be utilized. The computer readable medium may be a computer readable signal medium or a computer readable storage medium.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations, and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

Examples of the processors as described herein may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

Various additional details of embodiments of the present disclosure will be described below with reference to the figures. While the flowcharts will be discussed and illustrated in relation to a particular sequence of events, it should be appreciated that changes, additions, and omissions to this sequence can occur without materially affecting the operation of the disclosed embodiments, configuration, and aspects.

FIG. 1 is a block diagram illustrating elements of an exemplary computing environment in which embodiments of the present disclosure may be implemented. More specifically, this example illustrates a computing environment 100 that may function as the servers, user computers, or other systems provided and described herein. The environment 100 includes one or more user computers, or computing devices, such as a computing device 104, a communication device 108, and/or more 112. The computing devices 104, 108, 112 may include general purpose personal computers (including, merely by way of example, personal computers, and/or laptop computers running various versions of Microsoft Corp.'s Windows® and/or Apple Corp.'s Macintosh® operating systems) and/or workstation computers running any of a variety of commercially-available UNIX® or UNIX-like operating systems. These computing devices 104, 108, 112 may also have any of a variety of applications, including for example, database client and/or server applications, and web browser applications. Alternatively, the computing devices 104, 108, 112 may be any other electronic device, such as a thin-client computer, Internet-enabled mobile telephone, and/or personal digital assistant, capable of communicating via a network 110 and/or displaying and navigating web pages or other types of electronic documents. Although the exemplary computer environment 100 is shown with two computing devices, any number of user computers or computing devices may be supported.

Environment 100 further includes a network 110. The network 110 may can be any type of network familiar to those skilled in the art that can support data communications using any of a variety of commercially-available protocols, including without limitation SIP, TCP/IP, SNA, IPX, AppleTalk, and the like. Merely by way of example, the network 110 may be a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.9 suite of protocols, the Bluetooth® protocol known in the art, and/or any other wireless protocol); and/or any combination of these and/or other networks.

The system may also include one or more servers 114, 116. In this example, server 114 is shown as a web server and server 116 is shown as an application server. The web server 114, which may be used to process requests for web pages or other electronic documents from computing devices 104, 108, 112. The web server 114 can be running an operating system including any of those discussed above, as well as any commercially-available server operating systems. The web server 114 can also run a variety of server applications, including SIP (Session Initiation Protocol) servers, HTTP(s) servers, FTP servers, CGI servers, database servers, Java servers, and the like. In some instances, the web server 114 may publish operations available operations as one or more web services.

The environment 100 may also include one or more file and or/application servers 116, which can, in addition to an operating system, include one or more applications accessible by a client running on one or more of the computing devices 104, 108, 112. The server(s) 116 and/or 114 may be one or more general purpose computers capable of executing programs or scripts in response to the computing devices 104, 108, 112. As one example, the server 116, 114 may execute one or more web applications. The web application may be implemented as one or more scripts or programs written in any programming language, such as Java™, C, C#®, or C++, and/or any scripting language, such as Perl, Python, or TCL, as well as combinations of any programming/scripting languages. The application server(s) 116 may also include database servers, including without limitation those commercially available from Oracle®, Microsoft®, Sybase®, IBM® and the like, which can process requests from database clients running on a computing device 104, 108, 112.

The web pages created by the server 114 and/or 116 may be forwarded to a computing device 104, 108, 112 via a web (file) server 114, 116. Similarly, the web server 114 may be able to receive web page requests, web services invocations, and/or input data from a computing device 104, 108, 112 (e.g., a user computer, etc.) and can forward the web page requests and/or input data to the web (application) server 116. In further embodiments, the server 116 may function as a file server. Although for ease of description, FIG. 1 illustrates a separate web server 114 and file/application server 116, those skilled in the art will recognize that the functions described with respect to servers 114, 116 may be performed by a single server and/or a plurality of specialized servers, depending on implementation-specific needs and parameters. The computer systems 104, 108, 112, web (file) server 114 and/or web (application) server 116 may function as the system, devices, or components described herein.

The environment 100 may also include a database 118. The database 118 may reside in a variety of locations. By way of example, database 118 may reside on a storage medium local to (and/or resident in) one or more of the computers 104, 108, 112, 114, 116. Alternatively, it may be remote from any or all of the computers 104, 108, 112, 114, 116, and in communication (e.g., via the network 110) with one or more of these. The database 118 may reside in a storage-area network ("SAN") familiar to those skilled in the art. Similarly, any necessary files for performing the functions attributed to the computers 104, 108, 112, 114, 116 may be stored locally on the respective computer and/or remotely, as appropriate. The database 118 may be a relational database, such as Oracle 20i®, that is adapted to store, update, and retrieve data in response to SQL-formatted commands.

Figure 2:
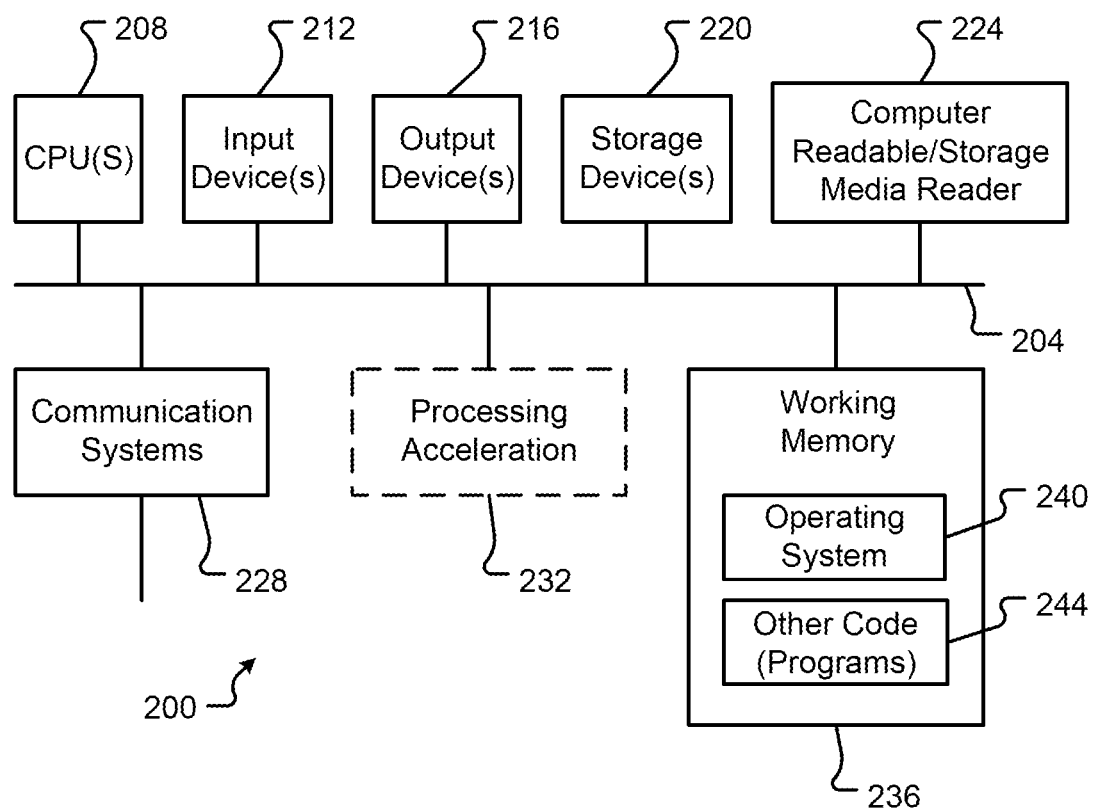
FIG. 2 is a block diagram illustrating elements of an exemplary computing device in which embodiments of the present disclosure may be implemented.

FIG. 2 is a block diagram illustrating elements of an exemplary computing device in which embodiments of the present disclosure may be implemented. More specifically, this example illustrates one embodiment of a computer system 200 upon which the servers, user computers, computing devices, or other systems or components described above may be deployed or executed. The computer system 200 is shown comprising hardware elements that may be electrically coupled via a bus 204. The hardware elements may include one or more central processing units (CPUs) 208; one or more input devices 212 (e.g., a mouse, a keyboard, etc.); and one or more output devices 216 (e.g., a display device, a printer, etc.). The computer system 200 may also include one or more storage devices 220. By way of example, storage device(s) 220 may be disk drives, optical storage devices, solid-state storage devices such as a random-access memory ("RAM") and/or a read-only memory ("ROM"), which can be programmable, flash-updateable and/or the like.

The computer system 200 may additionally include a computer-readable storage media reader 224; a communications system 228 (e.g., a modem, a network card (wireless or wired), an infra-red communication device, etc.); and working memory 236, which may include RAM and ROM devices as described above. The computer system 200 may also include a processing acceleration unit 232, which can include a DSP, a special-purpose processor, and/or the like.

The computer-readable storage media reader 224 can further be connected to a computer-readable storage medium, together (and, optionally, in combination with storage device(s) 220) comprehensively representing remote, local, fixed, and/or removable storage devices plus storage media for temporarily and/or more permanently containing computer-readable information. The communications system 228 may permit data to be exchanged with a network and/or any other computer described above with respect to the computer environments described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine-readable mediums for storing information.

The computer system 200 may also comprise software elements, shown as being currently located within a working memory 236, including an operating system 240 and/or other code 244. It should be appreciated that alternate embodiments of a computer system 200 may have numerous variations from that described above. For example, customized hardware might also be used and/or particular elements might be implemented in hardware, software (including portable software, such as applets), or both. Further, connection to other computing devices such as network input/output devices may be employed.

Examples of the processors 208 as described herein may include, but are not limited to, at least one of Qualcomm® Snapdragon® 800 and 801, Qualcomm® Snapdragon® 620 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

Figure 3:
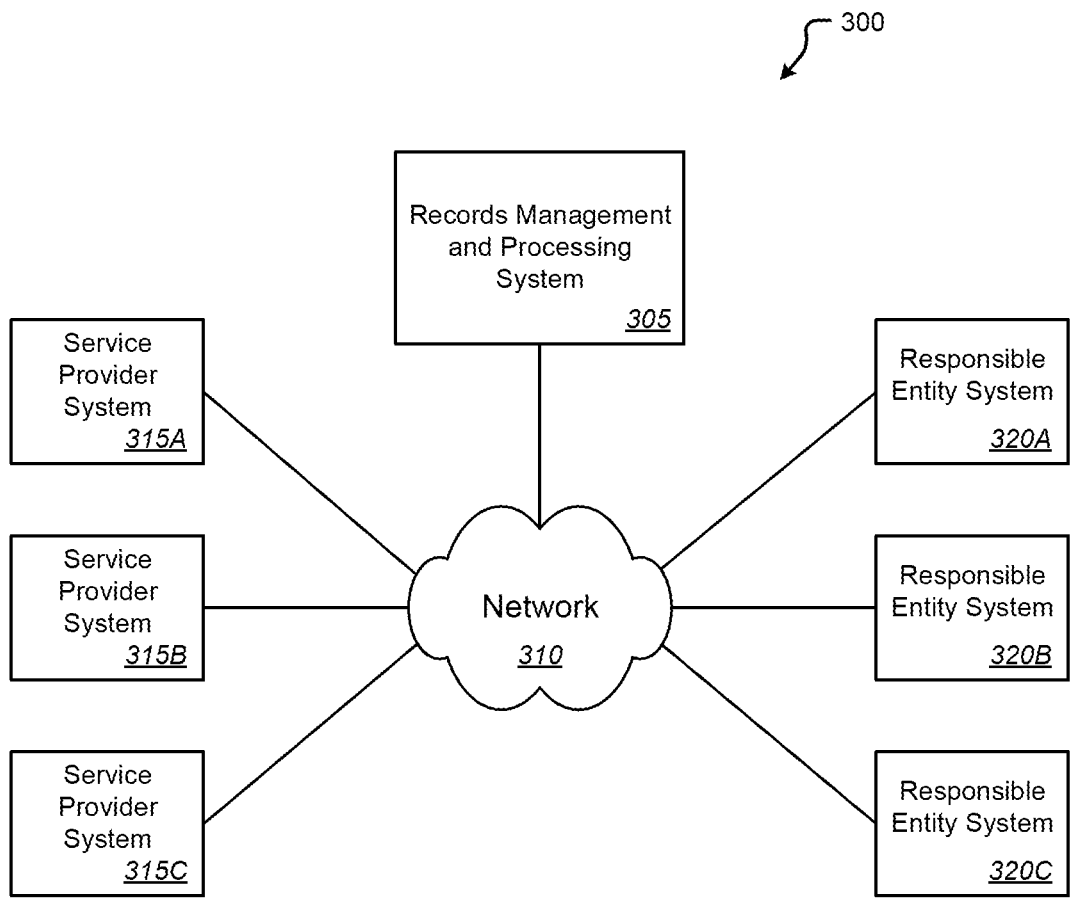
FIG. 3 is a block diagram illustrating an exemplary environment in which a records management and processing system and data collection service can be implemented according to one embodiment of the present disclosure.

FIG. 3 is a block diagram illustrating an exemplary environment in which a records management and processing system and data collection service can be implemented according to one embodiment of the present disclosure. As illustrated in this example, the environment 300 can include a number of different systems. Specifically, the environment 300 can include a records management and processing system 305 which can comprise a server or other computing device as described above. The records management and processing system 305 can be communicatively coupled with a communication network 310 such as the Internet or any other one or more wired or wireless, local or wide area networks. The environment 300 can also include a number of service provider systems 315A-315C each of which can comprise a server or other computing device as described above and which can also be communicatively coupled with the communication network 310. Furthermore, the environment 300 can include a number of responsible entity systems 320A-320C each of which can comprise a server or other computing device as described above and which can also be communicatively coupled with the communication network 310. It should be noted that while three service provider systems 315A-315C and three responsible entity systems 320A-320C are shown here for illustrative purposes, any number of such systems 315A-315C and 320A-320C can be present in various different implementations without departing from the scope of the present disclosure.

According to one implementation, the service provider systems 315A-315C can represent those servers or other computer systems typically associated with an entity providing a service consumer. In one embodiment, the providers of the services can comprise healthcare providers such as hospital, doctors, physical therapists, counsellors, out-patient and/or urgent care facilities, pharmacies, or other such providers while the consumer can comprise a patient. In such embodiments, the responsible party systems 320A-320C can comprise, for example, those servers or other computer systems typically associated with an entity responsible for some duties related to the delivery of and/or payment for those services. For example, responsible parties can include third-party payors including but not limited to insurance companies, Medicare, Medicaid, and/or other private, governmental, or mixed public/private entities. While described here with reference to healthcare providers and third-party payors such as insurance companies, it should be understood that various embodiments of the present disclosure are not limited to such implementations. Rather, embodiments of the present invention are believed to be equally adaptable to and useful in environments and systems which process a large volume of electronic records according to complex rules and regulations, business or financial arrangements, etc.

Regardless of the exact implementation of nature of the entities involved, the records management and processing system 305 can comprise an intermediary between a plurality of service providers systems 315A-315C and the plurality of responsible entity systems 320A-320C. As such and as will be described in greater detail below, the records management and processing system 305 can maintain a set of records related to services provided to a consumer by each or the service providers and for which at least one of the responsible entities is responsible in some way, e.g., granting approval, making a payment, providing some additional information, etc. In the normal course of processing such records and such transactions, the records management and processing system 305 may experience a delay in the handling of some records. For example, delays can be caused by data anomalies in records provided to the records management and processing system 305 by the service provider systems 315A-315C. In other cases, delays can be caused by a problem or potential problem with the handling of records or the performance of required actions by the responsible entity systems 320A-320C. In the example of the healthcare implementation described above, the records can represent, at least in part, payments to be made by the responsible entities to the service providers and thus, can represent accounts receivable for the service providers. As such, the timely completion of handling such records can directly impacts the cashflow of the service providers. Additionally, the longer processing of such records is delayed, the more likely the payments will become contested or otherwise become problematic. In other implementations, the timely processing of records by the records management and processing system 305 can be equally important for a variety of other reasons.

Accordingly, embodiments of the present disclosure are directed to methods and systems for the timely processing of records by the records management and processing system 305 exchanged between the service provider systems 315A-315C and the responsible entity systems 320A-320C. More specifically, the records management and processing system 305 can maintain a set of rules defining conditions for processing records and associated actions to affect that processing upon satisfaction of or failure to satisfy the conditions of that rule. The records management and processing system 305 can also maintain tags identifying data in a record, current status of processing of a record, or other information about the record. The records management and processing system 305 can apply the rules to the records and assign tags to the records based on the conditions defined in the applied rules. The records management and processing system 305 can then process the records according to workflows for processing the records based on the assigned tags and applied rules.

Figure 4:
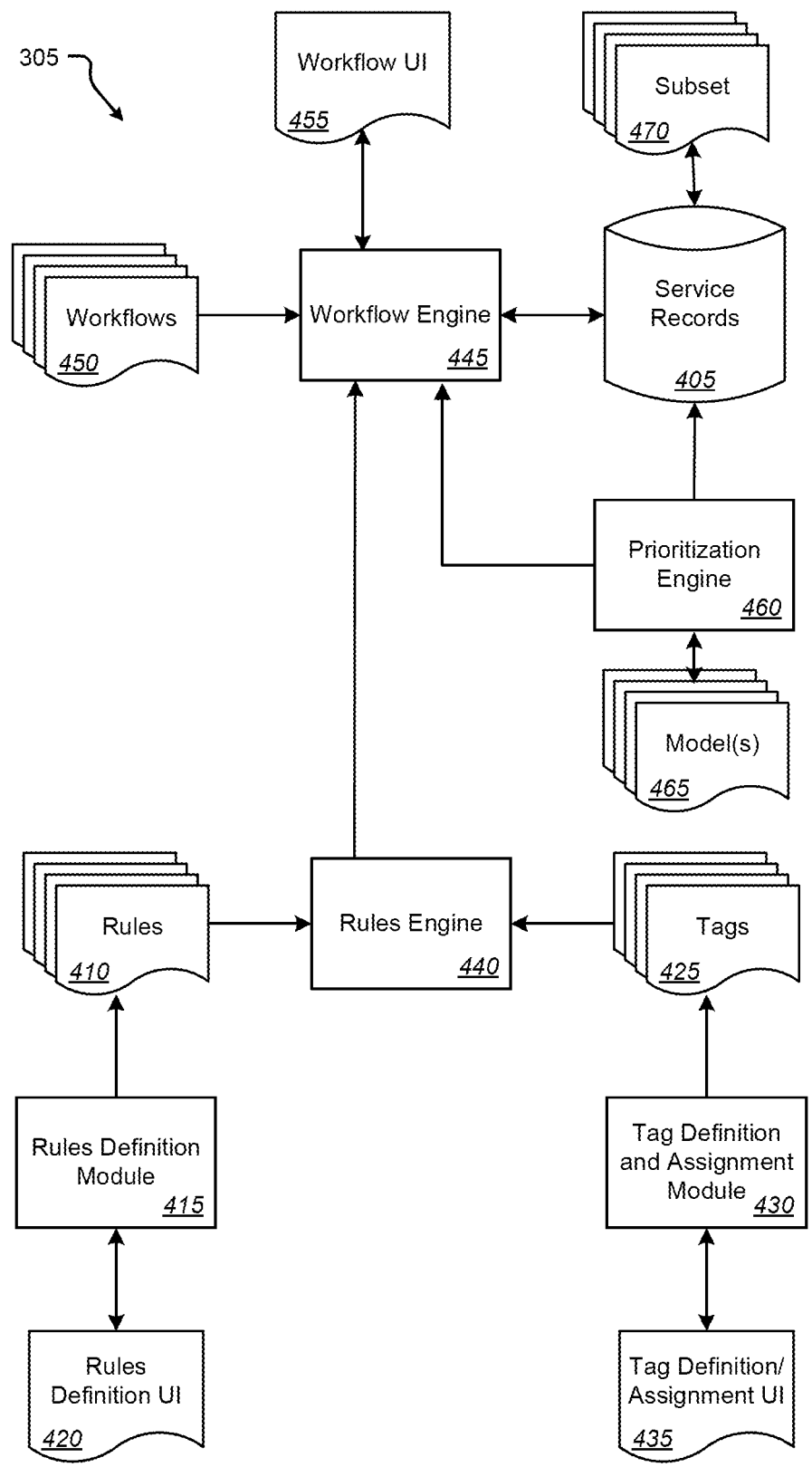
FIG. 4 is a block diagram illustrating elements of an exemplary records management and processing system according to one embodiment of the present disclosure.

FIG. 4 is a block diagram illustrating elements of an exemplary records management and processing system according to one embodiment of the present disclosure. As illustrated in this example, the records management and processing system 305 as described above can comprise a set of records maintained in a database 405 or other repository. As noted above, each record of the set of records in the database can comprise a record of a service provided to a consumer by a service provider and can identify at least one required action by at least one responsible entity of a plurality of responsible entities. Also, as described above, the records management and processing system 305 can comprise an intermediary between systems of the plurality of service providers and systems of the plurality of responsible entities.

The records management and processing system 305 can also maintain one or more rules 410 for managing and processing the records of the database 405. Generally speaking, a rule can comprise a definition of one or more conditions and an associated one or more actions to be performed upon satisfaction, or failure to satisfy, the conditions of that rule. Accordingly, each rule 410 maintained by the records management and processing system 305 can comprise one or more conditions for processing one or more records of the set of records 405 and at least one associated action to affect processing of the one or more records upon satisfaction of or failure to satisfy the one or more conditions of the rule 410. The conditions defined in some of these rules 410 can comprise conditions to be satisfied by one or more of the responsible entities 320A-320C described above. For example, one or more rules can define timing or other conditions a payment by a third-party payor, e.g., Medicare, Medicaid, an insurance company, etc., for a service rendered by the service provider, e.g., a hospital, doctor, pharmacy, etc., to the consumer/patient. Additionally, or alternatively, conditions defined in some of the rules 410 can define parameters for data in the record. For example, rules 410 can be defined for performing checks on the values of various fields of data in the records 405 such as comparing different fields, e.g., a value of total charges relative to a value of total adjustments, etc.

To facilitate definition of the rules 410, the records management and processing system 305 can further comprise a rules definition module 415. Generally speaking, the rules definition module 415 can comprise one or more applications executed by the records management and processing system 305 and which provide a rules definition interface 420. The rules definition interface 420 can include, for example, one or more webpages or other, similar interfaces providing elements through which an authorized user, such as an administrator or manager, can select or otherwise input conditions and corresponding actions for a new or modified rule. Once defined in this manner, the new or modified rule can be saved in the set of rules 410 and made available for application by the records management and processing system 305.

The records management and processing system 305 can also maintain a set of tags 425 for managing and processing the records 405. Generally speaking, these tags 425 can comprise a flag, metadata, or other information used to describe, explain, mark, or otherwise identify records in the set of records 405. For example, the tags 425 can include, but are not limited to, tags used to identify data in a record 405, a current status of processing of the record 405, or other information about the record. As will be described, these tags 425 can be used to identify records 405 that merit additional attention and/or processing and thus, the absence of tags associated with a record can implicitly indicate that additional attention or handling is not needed for that record.

To facilitate definition and use of the tags 425, the records management and processing system 305 can further comprise a tag definition and assignment module 430. Generally speaking, the tag definition and assignment module 430 can comprise one or more applications executed by the records management and processing system 305 and which provide a tag definition and assignment interface 435. The tag definition and assignment interface 435 can include, for example, one or more webpages or other, similar interfaces providing elements through which an authorized user, such as an administrator or manager, can select or otherwise input definitions of new or modified tags. Once defined in this manner, the new or modified tag can be saved in the set of tags 430 and made available for application by the records management and processing system 305.

The records management and processing system 305 can also comprise a rules engine 440. Generally speaking, the rules engine can comprise one or more applications executed by the records management and processing system 305 and which can read and apply the rules 410 to the records 405. That is, the rules engine 440 can compare the records stored in the database 405 to the conditions for the rules 410 and, upon finding records that satisfy, or fail to satisfy as the case may be and depending upon how the condition is defined, can perform or cause to be performed the action associated with the satisfied or failed condition. These actions can include, for example, applying one or more of the tags 425 to the identified records 405 or presenting the identified records to a user and receiving an indication of the tag(s) to be applied. The tag(s) 425 applied to a record can identify or mark that record for further attention to advance the processing of that record. Thus, records that are not tagged do not require additional attention or processing outside of normal processes since they are in a condition as defined in the rules as being normal or acceptable, e.g., within defined deadlines or other time limits etc. In other words, processing can be applied to one set of records based on the tags applied while processing of another set of records can be postponed or delayed so that the first set of records can be given more attention and resources.

The rules engine 440 can apply the rules 410 to the records 405 periodically, on demand, or upon the occurrence of predefined event or the satisfaction of one or more predefined conditions. For example, the rules engine 440 can apply the rules 410 as part of a routine process performed each day, week, month, or other period, and/or may be initiated or kicked off upon request by an authorized user of the system such as a manager or supervisor. As noted above, applying the rules 410 can include tagging one or more records based on the applied rules 410. Additionally, or alternatively, tags can be applied to one or more records based on a user selection or input. For example, a user viewing a set of records can select records from that set and apply one or more tags to those selected records based on conditions the user perceives and which may or may not be defined in the rules. Thus, tagging of records can be driven by the applied rules or based on input from a user and the tags applied in either way can influence the further handling of those tagged records.

According to one embodiment and as illustrated here, the records management and processing system 305 can also comprise a workflow engine 445 and a set of predefined workflows 450. Generally speaking, a workflow 450 can comprise a set of one or more steps to be performed on or related to a record. These steps can be wholly machine executable or may, in some cases, rely on some degree of human intervention. For example, these steps can range from presenting data from a tagged record in a user interface to a human operator, such as a collector, for an action to be performed by the operator, e.g., calling a payor or performing some other follow-up action, to a completely automated process such as sending an automatically generated communication to a payor system or combinations of various such human and machine actions. The workflow engine 445 can comprise one or more applications executed by the records management and processing system 305 and which, during execution, can read the predefined workflows 450 and implement or perform the steps defined therein. The workflows 450 can comprise a set of predefined, executable steps directed to advancing the processing of the records 405 identified by the rules 405 and tagged as described above. The workflow engine 445 can execute the workflows 450 by selecting a workflow 450 based on the tags 425 for a record 405 and executing the selected workflow 450 using the information from that record and, in some cases, based on further application of one or more rules 410 related to the tags 425 applied to that record 405. Thus, the conditions and associated actions defined in the rules 410 can also be applied by the workflow engine 445 as it executes the workflows 450. The workflow engine 445 can also provide a workflow user interface 450 for viewing and managing one or more workflows for processing records.

Therefore, the rules engine 440 can apply one or more of the rules 410 to the records saved in the database 405 to identify those records which should be further processed or given further scrutiny and mark those records with one or more tags 425. In this way, those records found to be within normal or acceptable conditions according to the applied rules need not be subjected to further scrutiny and/or processing thus saving resources such as human effort, processing overhead, etc. In other words, processing of one set of records can be performed in an expedited or priority manner while processing of another set of records can be de-prioritized or postponed based on the tags applied to the records which is in turn based on the rules or input from a user.

One or more predefined workflow processes 450 can then be selected, e.g., based on the applied tags, initiated, and executed by the workflow engine 445 to further process those tagged records. The workflows 450 can be initiated automatically, e.g., triggered by the rules engine 445 upon completion of applying the tags 425, upon the occurrence of certain conditions, e.g., as defined in one or more rules 410, at a predetermined or pre-scheduled time, upon request, or in a variety of other ways without departing from the scope of the present disclosure. Processing the tagged records 405 by the workflow engine 445 can comprise performing the steps defined in the workflows 450, which can include applying the selected or additional rules 410 to the records being processed, in order to advance the handling of those records 405 by the records management and processing system 305, e.g., move an account towards payment or other resolution.

To further facilitate this processing of the records 405 the records management and processing system 305 can further include an annotation engine 460. Generally speaking, the annotation engine 460 can be adapted to add notes or other annotations to the records 405. For example, the annotation engine 460 can present an user interface 465. Through such interfaces, a user may add a note or other annotation to the record to indicate, for example, a current status of the record, an action taken on the record, an action required or to be taken on the record, etc. According to one embodiment, and to facilitate the making of such annotations, these annotations can be collected as part of a dynamic query session. As used herein, the term dynamic query session is intended to mean a process conducted by the annotation engine 460 through which information related to one or more records of interest is collected from one or more sources. These sources can be one or more users of the records processing and management system 305, the record of interest itself and/or other records in the plurality of records 405, and/or other sources accessible by the records processing and management system 405 including but not limited to users, records, and/or services of other systems such as a of other systems such as a service provider system 315, a responsible entity system 320, etc. The dynamic query session can be conducted in the form of a question-and-answer session in which questions are posed to users and/or form the basis of a database query on the records 405 or calls to systems or services of other systems. These queries are referred to as dynamic in that the answer obtained for one query can change or influence a subsequent query presented. For example, the questions to be posed or queries to be made in a session can be arranged as part of a decision tree or similar structure that can be navigated as answers or information are obtained.

To implement such a dynamic query session, the annotation engine 460 can be adapted to define and utilize a set of note templates 470. Generally speaking, each template 470 can define a dynamic query session for a particular condition on a record or set of records, e.g., a value of a field of the record, aging of the record, etc. Each template 470 can also identify one or more actions to be taken based on results of the dynamic query session, i.e., based on the answers collected. These actions can be defined, for example, in one or more rules 410 and implementing those actions can additionally, or alternatively, comprise initiating a workflow 450 as described above, for example. Each template 470 can also define a format and content for an annotation to be added to a record for which the dynamic query session is executed. The annotation can include both predefined text as well as answers or results obtained by the dynamic query session.

With multiple workflows 450 and/or work queues and rules 410 running in parallel, sub-optimal management and prioritization of records being processed may occur. Embodiments of the present disclosure are directed to prioritizing the processing of selected records 405. For example, and returning to the healthcare example described herein, embodiments may prioritize non-zero (debit balance) insurance balance AR & Denial accounts utilizing the current status of the accounts and expected outcome to maximize yield, e.g., net insurance payment amount on the account, and reduce non-yield resulting touches.

According to one embodiment, managing and processing database records 405 can comprise maintaining a plurality of records 405 in a database as described above. A subset of records 470 can be identified or selected from the plurality of records 405 by a prioritization engine 460. The identified subset of records 470 can comprise a plurality of records to be further processed by the records management and processing system 305. Identifying the subset of records 470 from the plurality of records can be based on a value stored in a field of each record of the plurality of records 405. For example, identifying a record of the subset of records can be based on the value stored in the field of the record being greater than zero, e.g., a non-zero AR balance.

Each record of the identified subset of records 470 can be scored by the prioritization engine 460 based on a plurality of factors related to each record of the identified subset of records 470. According to one embodiment, the plurality of factors related to each record can comprise a current status for the record. In such cases, scoring each record of the identified subset of records can comprise determining a status score based on the current status for the record. This allows the prioritization engine 460 to add priority/urgency to accounts based on their current status. For example, the status score can be based on a pre-defined adjustable list of statuses and scores.

Additionally, or alternatively, the plurality of factors related to each record can comprise an expected yield factor. The expected yield factor can represent a probability of a benefit obtained from further processing of the record. The yield factor can be determined, for example, based on one or more models 465 trained on results of previous processing of the plurality of records. In such cases, scoring each record of the identified subset of records can comprise determining a yield score based on the yield factor. According to one embodiment, the higher the expected yield on the account from the models 465, the higher the yield score can be on the record. In the healthcare example, features the models 465 can use to calculate the expected yield can include, but are not limited to, account balance, payor category, account aging, patient demographics, payments and adjustments, patient coding, and/or others.

The plurality of factors related to each record can additionally, or alternatively, comprise a time factor representing an amount of time since a last processing of the record. In such cases, scoring each record of the identified subset of records can comprise determining a touch score based on the time factor. This allows the prioritization engine 460 to give higher weightage to the accounts that haven't been touched/revisited/processed in a long period.

Additionally, or alternatively, the plurality of factors related to each record can comprise an age factor representing a pendency period of time for the record. In such cases, scoring each record of the identified subset of records can comprise determining a discharge score based on the age factor. In the healthcare example, the longer the account ages post patient discharge, the prioritization engine 460 can add a higher weightage to the final discharge score of the record.

Scoring each record of the identified subset of records can then comprise determining a sum of the status score, the yield score, the touch score, and the discharge score for each record of the identified subset of records 470.

The identified subset of records can then be prioritized by the prioritization engine 460 into an ordered list of records based on the score for each record of the identified subset of records 470 and one or more workflows 450 can be executed on the identified subset of records based on the ordered list of records.

Figure 5:
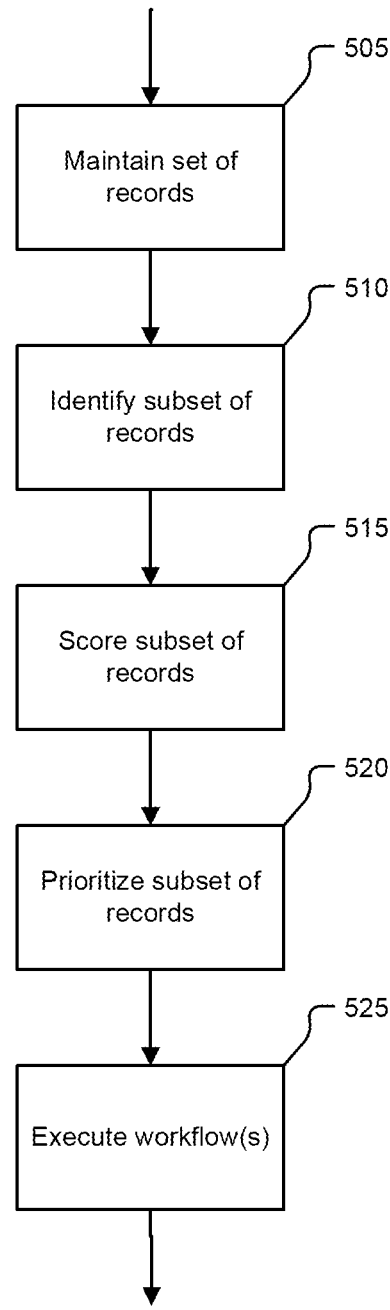
FIG. 5 is a flowchart illustrating an exemplary process for processing database records based on a determined priority for selected database records according to one embodiment of the present disclosure.

FIG. 5 is a flowchart illustrating an exemplary process for processing database records based on a determined priority for selected database records according to one embodiment of the present disclosure. As illustrated in this example, managing and processing database records can comprise maintaining 505 a plurality of records in a database. Each record of the plurality of records can comprise a record of a service provided to a consumer by a service provider of a plurality of service providers and can identify at least one required action by at least one responsible entity of a plurality of responsible entities.

A subset of records from the plurality of records can be identified 510. The identified 510 subset of records can comprise a plurality of records to be further processed by the records management and processing system. Identifying 510 the subset of records from the plurality of records can be based on a value stored in a field of each record of the plurality of records. For example, identifying 510 a record of the subset of records can be based on the value stored in the field of the record being greater than zero.

Each record of the identified subset of records can be scored 515 based on a plurality of factors related to each record of the identified subset of records. Additional details of an exemplary process for scoring 515 each record of the subset of records will be described below with reference to FIG. 6. The identified subset of records can then be prioritized 520 into an ordered list of records based on the score for each record of the identified subset of records and one or more workflows can be executed 525 on the identified subset of records based on the ordered list of records.

Figure 6:
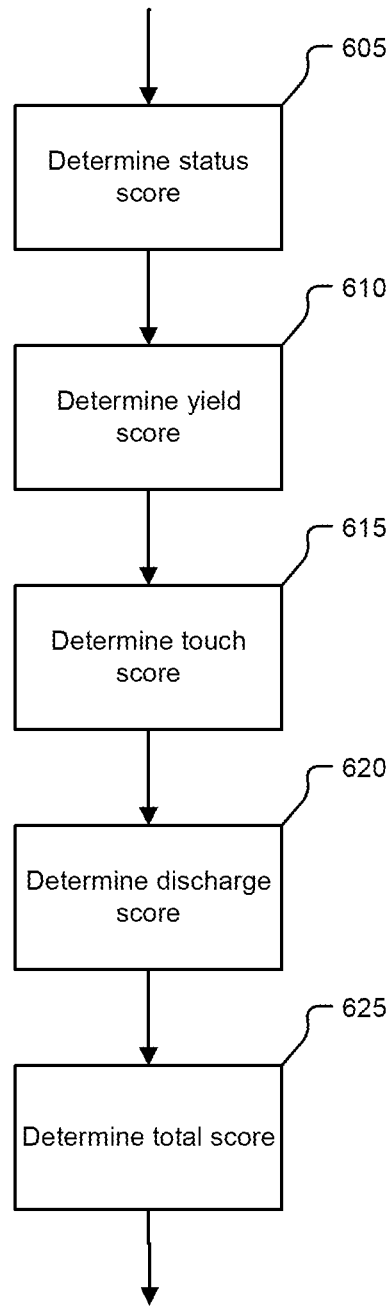
FIG. 6 is a flowchart illustrating an exemplary process for scoring of selected database records according to one embodiment of the present disclosure.

FIG. 6 is a flowchart illustrating an exemplary process for scoring of selected database records according to one embodiment of the present disclosure. It should be noted that while illustrated and described here as a sequence of processes, an order of the processes should not be inferred. Rather, these processes can be performed in various orders or in parallel depending upon the implementation. According to one embodiment, the plurality of factors related to each record can comprise a current status for the record. In such cases and as illustrated in this example, scoring each record of the identified subset of records can comprise determining 605 a status score based on the current status for the record.

Additionally, or alternatively, the plurality of factors related to each record can comprise an expected yield factor. The expected yield factor can represent a probability of a benefit obtained from further processing of the record. The yield factor can be determined, for example, based on a model trained on results of previous processing of the plurality of records. In such cases, scoring each record of the identified subset of records can comprise determining 610 a yield score based on the yield factor.

The plurality of factors related to each record can additionally, or alternatively, comprise a time factor representing an amount of time since a last processing of the record. In such cases, scoring each record of the identified subset of records can comprise determining 615 a touch score based on the time factor.

Additionally, or alternatively, the plurality of factors related to each record can comprise an age factor representing a pendency period of time for the record. In such cases, scoring each record of the identified subset of records can comprise determining 620 a discharge score based on the age factor. Scoring each record of the identified subset of records can then comprise determining 625 a sum of the status score, the yield score, the touch score, and the discharge score for each record of the identified subset of records.

The present disclosure, in various aspects, embodiments, and/or configurations, includes components, methods, processes, systems, and/or apparatus substantially as depicted and described herein, including various aspects, embodiments, configurations embodiments, sub-combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving case and/or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for managing and processing database records, the method comprising:
   maintaining, by a records management and processing system, a plurality of records in a database, each record of the plurality of records comprising a record of a service provided to a consumer by a service provider of a plurality of service providers and identifying at least one required action by at least one responsible entity of a plurality of responsible entities and wherein the records management and processing system comprises an intermediary between systems of the plurality of service providers and systems of the plurality of responsible entities;
   identifying, by the records management and processing system, a subset of records from the plurality of records, the subset of records comprising a plurality of records to be further processed by the records management and processing system;
   scoring, by the records management and processing system, each record of the identified subset of records based on a plurality of factors related to each record of the identified subset of records, wherein scoring each record of the identified subset of records is based on a plurality of scores, wherein the plurality of scores comprises a score for each of the plurality of factors, and wherein the plurality of scores comprises a status score, a yield score, a touch score, and a discharge score;
   prioritizing, by the records management and processing system, the identified subset of records into an ordered list of records based on the score for each record of the identified subset of records; and
   executing, by the records management and processing system, one or more workflows on the identified subset of records based on the ordered list of records.

2. The method of claim 1, wherein identifying the subset of records from the plurality of records is based on a value stored in a field of each record of the plurality of records and wherein identifying a record of the subset of records is based on the value stored in the field of the record being greater than zero.

3. The method of claim 1, wherein the plurality of factors related to each record comprises a current status for the record and wherein scoring each record of the identified subset of records comprises determining the status score based on the current status for the record.

4. The method of claim 3, wherein the plurality of factors related to each record comprises an expected yield factor, wherein the expected yield factor represents a probability of a benefit obtained from further processing of the record, wherein the yield factor is determined based on a model trained on results of previous processing of the plurality of records, and wherein scoring each record of the identified subset of records comprises determining the yield score based on the yield factor.

5. The method of claim 4, wherein the plurality of factors related to each record comprises a time factor representing an amount of time since a last processing of the record and wherein scoring each record of the identified subset of records comprises determining the touch score based on the time factor.

6. The method of claim 5, wherein the plurality of factors related to each record comprises an age factor representing a pendency period of time for the record and wherein scoring each record of the identified subset of records comprises determining the discharge score based on the age factor.

7. The method of claim 6, wherein scoring each record of the identified subset of records comprises determining a sum of the status score, the yield score, the touch score, and the discharge score for each record of the identified subset of records.

8. A system comprising:
a processor; and
a memory coupled with and readable by the processor and storing therein a set of instructions which, when executed by the processor, causes the processor to manage and process database records by:
maintaining a plurality of records in a database, each record of the plurality of records comprising a record of a service provided to a consumer by a service provider of a plurality of service providers and identifying at least one required action by at least one responsible entity of a plurality of responsible entities and wherein the records management and processing system comprises an intermediary between systems of the plurality of service providers and systems of the plurality of responsible entities;
identifying a subset of records from the plurality of records, the subset of records comprising a plurality of records to be further processed by the records management and processing system;
scoring each record of the identified subset of records based on a plurality of factors related to each record of the identified subset of records, wherein scoring each record of the identified subset of records is based on a plurality of scores, wherein the plurality of scores comprises a score for each of the plurality of factors, and wherein the plurality of scores comprises a status score, a yield score, a touch score, and a discharge score;
prioritizing the identified subset of records into an ordered list of records based on the score for each record of the identified subset of records; and
executing one or more workflows on the identified subset of records based on the ordered list of records.

9. The system of claim 8, wherein identifying the subset of records from the plurality of records is based on a value stored in a field of each record of the plurality of records and wherein identifying a record of the subset of records is based on the value stored in the field of the record being greater than zero.

10. The system of claim 8, wherein the plurality of factors related to each record comprises a current status for the record and wherein scoring each record of the identified subset of records comprises determining the status score based on the current status for the record.

11. The system of claim 10, wherein the plurality of factors related to each record comprises an expected yield factor, wherein the expected yield factor represents a probability of a benefit obtained from further processing of the record, wherein the yield factor is determined based on a model trained on results of previous processing of the plurality of records, and wherein scoring each record of the identified subset of records comprises determining the yield score based on the yield factor.

12. The system of claim 11, wherein the plurality of factors related to each record comprises a time factor representing an amount of time since a last processing of the record and wherein scoring each record of the identified subset of records comprises determining the touch score based on the time factor.

13. The system of claim 12, wherein the plurality of factors related to each record comprises an age factor representing a pendency period of time for the record and wherein scoring each record of the identified subset of records comprises determining the discharge score based on the age factor.

14. The system of claim 13, wherein scoring each record of the identified subset of records comprises determining a sum of the status score, the yield score, the touch score, and the discharge score for each record of the identified subset of records.

15. A non-transitory, computer-readable medium comprising a set of instructions stored therein which, when executed by the processor, causes the processor to maintain and process database records by:
maintaining a plurality of records in a database, each record of the plurality of records comprising a record of a service provided to a consumer by a service provider of a plurality of service providers and identifying at least one required action by at least one responsible entity of a plurality of responsible entities and wherein the records management and processing system comprises an intermediary between systems of the plurality of service providers and systems of the plurality of responsible entities;
identifying a subset of records from the plurality of records, the subset of records comprising a plurality of records to be further processed by the records management and processing system;
scoring each record of the identified subset of records based on a plurality of factors related to each record of the identified subset of records, wherein scoring each record of the identified subset of records is based on a plurality of scores, wherein the plurality of scores comprises a score for each of the plurality of factors, and wherein the plurality of scores comprises a status score, a yield score, a touch score, and a discharge score;
prioritizing the identified subset of records into an ordered list of records based on the score for each record of the identified subset of records; and
executing one or more workflows on the identified subset of records based on the ordered list of records.

16. The non-transitory, computer-readable medium of claim 15, wherein identifying the subset of records from the plurality of records is based on a value stored in a field of each record of the plurality of records and wherein identifying a record of the subset of records is based on the value stored in the field of the record being greater than zero.

17. The non-transitory, computer-readable medium of claim 15, wherein the plurality of factors related to each record comprises a current status for the record and wherein scoring each record of the identified subset of records comprises determining the status score based on the current status for the record.

18. The non-transitory, computer-readable medium of claim 17, wherein the plurality of factors related to each record comprises an expected yield factor, wherein the expected yield factor represents a probability of a benefit obtained from further processing of the record, wherein the yield factor is determined based on a model trained on results of previous processing of the plurality of records, and wherein scoring each record of the identified subset of records comprises determining the yield score based on the yield factor.

19. The non-transitory, computer-readable medium of claim 18, wherein the plurality of factors related to each record comprises a time factor representing an amount of time since a last processing of the record and wherein scoring each record of the identified subset of records comprises determining the touch score based on the time factor.

20. The non-transitory, computer-readable medium of claim 19, wherein the plurality of factors related to each record comprises an age factor representing a pendency period of time for the record, wherein scoring each record of the identified subset of records comprises determining the discharge score based on the age factor, and wherein scoring each record of the identified subset of records comprises determining a sum of the status score, the yield score, the touch score, and the discharge score for each record of the identified subset of records.

\* \* \* \* \*